(12) United States Patent
Bosch et al.

(10) Patent No.: US 6,320,395 B1
(45) Date of Patent: Nov. 20, 2001

(54) APPARATUS AND METHOD FOR ELECTROCHEMICAL CORROSION MONITORING

(75) Inventors: Rik-Wouter Bosch, Veldhoven (NL); Walter F. Bogaerts, Geel (BE)

(73) Assignee: Katholieke Universiteit Leuven, Leuven (BE)

( * ) Notice: Subject to any disclaimer, the term of this patent is extended or adjusted under 35 U.S.C. 154(b) by 0 days.

(21) Appl. No.: 09/546,728

(22) Filed: Apr. 11, 2000

Related U.S. Application Data (60) Provisional application No. 60/139,553, filed on Jun. 16, 1999.

(51) Int. Cl.[7] .................................................. G01R 27/08
(52) U.S. Cl. ................................................................ 324/700
(58) Field of Search ................................... 324/700, 71.1, 324/71.2, 718, 713; 204/404; 205/775.5; 422/53

(56) References Cited

U.S. PATENT DOCUMENTS

| | | | |
|---|---|---|---|
| 4,658,365 | 4/1987 | Syrett et al. | 364/496 |
| 5,006,786 | 4/1991 | McKubre et al. | 324/71.2 |

FOREIGN PATENT DOCUMENTS

| | | | |
|---|---|---|---|
| 1293770 | 6/1988 | (CA) | 204/115 |
| 0246029A2 | 5/1987 | (EP) | G01N/17/00 |
| 0287348A2 | 10/1988 | (EP) | G01N/17/00 |

OTHER PUBLICATIONS

Bosch, R.W., et al., "Instantaneous Corrosion Rate Measurement With Small–Amplitude Intermodulation Techniques" Corrosion–Mar. 1996 vol. 52, Nov. 3, 1996, pp. 204–212.

Bosch et al. "The Small Amplitude Potential Intermodulation Technique for the Monitoring of Corrosion Inhibition," *CORR Session II*, Sep. 24–26, 1996.

Meszaros et al., "Study of the Rate of Corrosion of Metals by a Faradaic Distortion Method, III," *Acta Chim. Acad. Sci. Hung.* 105, 1980.

Rao et al., "A.C. Techniques to Evaluate the Kinetics of Corrosion Reactions," *J. Electroanal. Chem.*, 77 (1977) pp. 121–125.

U. Bertocci, "AC Induced Corrosion. The Effect of an Alternating Voltage on Electrodes Under Charge–Transfer Control," *Corrosion–Nace*, vol. 35, No. 5, May 1979 pp. 211–215.

*Primary Examiner*—Safet Metjahic
*Assistant Examiner*—J Kerveros
(74) *Attorney, Agent, or Firm*—Flehr Hohbach Test Albritton & Herbert LLP (57) ABSTRACT

A method and apparatus are provided for monitoring a corrosion current density to determine a corrosion rate of a corroding system 130 using Electrochemical Frequency Modulation (EFM). In the method two sinusoidal signals 100, 105, having different frequencies are applied to a portion of the system 130 to distort a response current 120 in the system. Analysis of this current 120 generated in response to the applied perturbation signal 110 provides the corrosion rate and Tafel parameters of the system 130 without prior knowledge of the Tafel parameters. In one embodiment, the method and apparatus also provide a mechanism for validating the quality of the measured data used in calculating the corrosion rate and Tafel parameters.

17 Claims, 9 Drawing Sheets

APPARATUS AND METHOD FOR ELECTROCHEMICAL CORROSION MONITORING

CROSS REFERENCE TO RELATED APPLICATIONS

This application claims priority from U.S. Provisional Patent Application Serial No. 60/139,553 filed Jun. 16, 1999, which is incorporated herein by reference.

FIELD OF THE INVENTION

The present invention relates generally to a method of monitoring aqueous corrosion of metals, and more particularly to a method of monitoring employing electrochemical frequency modulation with the capability of validating data quality.

BACKGROUND OF THE INVENTION

Aqueous corrosion of metals is an electrochemical process involving anodic oxidation of a metal in a solution and cathodic reduction of species from the solution. This process is often monitored using an electrochemical technique, such as Linear Polarization Resistance (LPR), Tafel extrapolation and Electrochemical Impedance Spectroscopy (EIS). However, all of these techniques suffer from one or more significant drawbacks. For example, the LPR and EIS techniques can be used for instantaneous corrosion rate measurements only if the anodic and cathodic Tafel parameters ($b_a$ and $b_c$, respectively) are known. The Tafel extrapolation technique permit determination of the corrosion rate and the Tafel parameters but is not suitable for instantaneous corrosion rate measurements because the system must be polarized over a wide potential range such that the measurement is time consuming and the surface of the metal is affected by the measurement.

Other electrochemical techniques rely on the fact that the corrosion process is non-linear, and that applying one or more sinusoidal signals will generate a response current at more frequencies than the frequencies of the applied signal. Thus, the corrosion rate can be determined by measuring a response current to the sinusoidal signals. One of these techniques, known as the Faraday rectification technique, involves measuring the response current at a "zero" frequency, that is measuring a direct current (DC). The Faraday rectification technique can be used if at least one of the Tafel parameters is known. Another technique, known as harmonic analysis, enables the corrosion rate and both Tafel parameters to be obtained with one measurement by analyzing the harmonic frequencies. Harmonic analysis has been used for corrosion rate measurements in acid media with and without inhibitors. A special application of harmonic analysis is Harmonic Impedance Spectroscopy (HIS), where the harmonic current components are transformed to harmonic impedances. HIS has been used to measure corrosion rates of polarized systems.

In corrosion research, virtually no attention has been given to intermodulation techniques. With the intermodulation technique one or more sinusoidal signals of different frequencies are applied to a corroding system and response currents measured. The alternating current (AC) responses include response currents at harmonics or multiples of the frequencies of the applied signals ($\omega_1$, $2\omega_1$, $3\omega_1$, ..., $\omega_2$, $2\omega_2$, $3\omega_2$, ...), and response currents at the intermodulation frequencies ($\omega_1 \pm \omega_2$, $2\omega_1 \pm \omega_2$, $2\omega_2 \pm \omega_1$ ...). With the intermodulation technique, just as with harmonic analysis, it is possible to determine a corrosion rate without prior knowledge of the Tafel parameters. The intermodulation technique as such has been used satisfactorily in semiconductor research. However, until now the intermodulation technique has never been successfully used for monitoring corrosion rates.

A further problem with all of the above techniques is that they do not provide a way to validate the measured response currents. Small currents have to be measured to determine a corrosion rate. These currents are easily influenced by background noise or any other kind of (electrical) disturbance. Using improperly measured data for the calculation of a corrosion rate can result in misleading results. In case of under estimation of corrosion rate, without a mechanism for validating the measured data an error in determining the corrosion rate is often not discovered until considerable damage has been done.

Accordingly, there is a need for a method and apparatus for quickly and continuously monitoring a corrosion rate of a corroding system without prior knowledge of Tafel parameters of the system. There is also a need for a method and apparatus for determining the Tafel parameters of the system. There is a further need for a mechanism for validating the measured data used to calculate the corrosion rate.

SUMMARY OF THE INVENTION

An object of the present invention is to provide a method and apparatus for monitoring a corrosion current density to determine a corrosion rate of a corroding system. The method including the step of applying two sinusoidal signals having different frequencies to a portion of the system, measuring a response current in response to the sinusoidal voltages, and analyzing the response current measured at zero, harmonic and intermodulation frequencies to obtain the corrosion rate.

Generally, the method includes the steps of applying two sinusoidal signals having different frequencies to a portion of the system, measuring a response current in response to the sinusoidal signals, and analyzing the response current measured at zero, harmonic and intermodulation frequencies to obtain the corrosion rate. According to one embodiment, the two sinusoidal signals have angular frequencies $\omega_1$ and $\omega_2$ and the step of analyzing the response current includes the steps of transforming the response current from a time domain to a frequency domain, and calculating the corrosion rate using one of the following equations:

$$i_{corr} = \frac{i_{\omega1\omega2}^2}{2\sqrt{8 i_{\omega1\omega2} i_{2\omega2\pm w1} - 3 i_{\omega2\pm\omega1}^2}}, \quad i_{corr} = \frac{i_{\omega1\omega2}^2}{2 i_{\omega2\pm\omega1}}$$

Optionally, the step of analyzing the response current includes the steps of analyzing the response current to obtain at least one Tafel parameter and to validate the quality of the measurements made. The step of validating the quality of the measurements includes the steps of calculating a causality factor using the response current measured at an intermodulation frequency and at a harmonic frequency of one of the two applied sinusoidal signals, and comparing the causality factor to a predetermined value. In one embodiment, the predetermined value is 2, and the causality factor is calculated using the following equation:

Causality factor 2: $\frac{i_{\omega 2 \pm \omega 1}}{i_{2\omega 1}}$

In another embodiment, the predetermined value is 3, and the causality factor is calculated using the following equation:

Causality factor 3: $\frac{i_{\omega 2 \pm \omega 1}}{i_{3\omega 1}}$

In another aspect, the present invention is directed to a computer program for monitoring a corrosion rate of a corroding system. The computer program includes a sinewave-generator module for generating and applying at least two sinusoidal signals having different frequencies to a portion of the system. A measured-waveform module for measuring voltages of the sinusoidal signals and a response current generated in the system in response to the signals. A frequency-response-magnitude module for transforming the measured response current from a time domain to a frequency domain. And a frequency-response-analyzer module for analyzing the response current to obtain the corrosion rate. Generally, the response current is measured at zero, harmonic and intermodulation frequencies of the sinusoidal signals. In one embodiment, the frequency-response-analyzer module is further configured to analyze the response current at harmonic and intermodulation frequencies of the sinusoidal signals to validate the quality of measurements made by the measured-waveform module. In another embodiment, it is also configured to analyze the response current to obtain one or more of the Tafel parameters for the system.

BRIEF DESCRIPTION OF THE DRAWINGS

These and various other features and advantages of the present invention will be apparent upon reading of the following detailed description in conjunction with the accompanying drawings, where.

DETAILED DESCRIPTION OF THE INVENTION

Figure 1A:
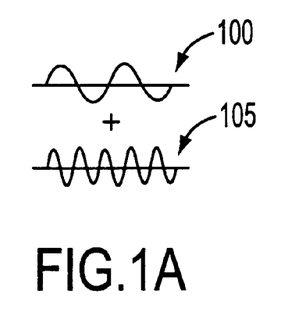
FIGS. 1A to 1C schematically illustrate sinusoidal perturbation signals suitable for monitoring corrosion according to an embodiment of the present invention.
Figure 1B:
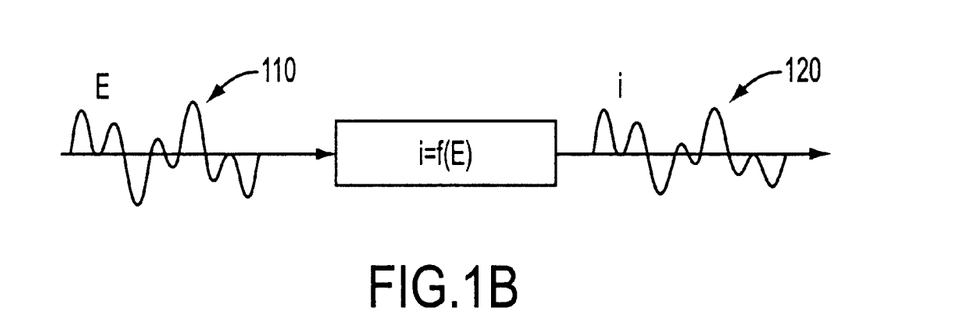
Figure 1C:
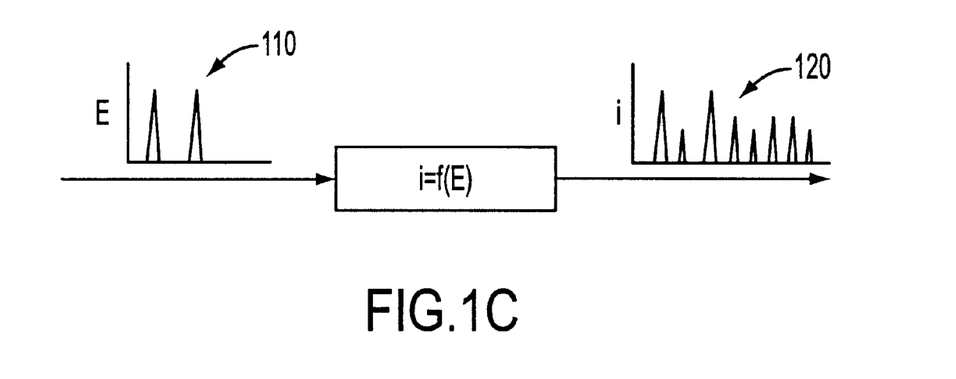

A method and apparatus are provided for monitoring a corrosion rate of a corroding system using an Electrochemical Frequency Modulation (EFM) technique. With the EFM technique, a potential perturbation or signal consisting of one or more sinusoidal waves of different frequencies is applied to the corroding system. An AC current generated in the corroding system in response to this signal consists of current components (peaks) of different frequencies. Because the corrosion process is non-linear in nature, the response current is made up of more frequencies than the frequencies of the applied signal. This response current is then measured and analyzed to determine the corrosion rate and other parameters of the corroding system. A simplified theoretical basis of the EFM-technique will now be described with reference to FIGS. 1A through 1C and FIGS. 2A and 2b. Referring to FIG. 1A, two sinusoidal signals 100, 105, are combined to create an intermodulation perturbation signal 110, E, described by the following equation:

$$E = U_o \sin \omega_1 t + U_o \sin \omega_2 t = U_o \sin 2\pi f_1 t + U_o \sin 2\pi f_2 t \quad (1.1)$$

where t is time, $U_o$ is the amplitude of the perturbation, $\omega_1$ and $\omega_2$ are the angular frequencies of the two sinusoidal signals and $f_1$ and $f_2$ are the same frequencies in Hertz.

Figure 2A:
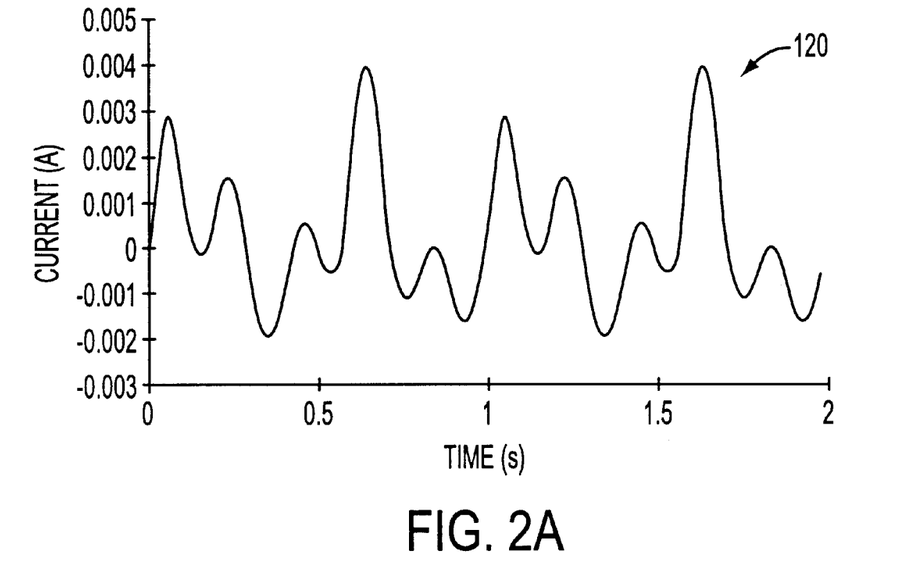
FIGS. 2A and 2B are graphs of computer simulations showing a response current generated in a corroding system in response to signals applied to the system in accordance with an embodiment of the present invention.
Figure 2B:
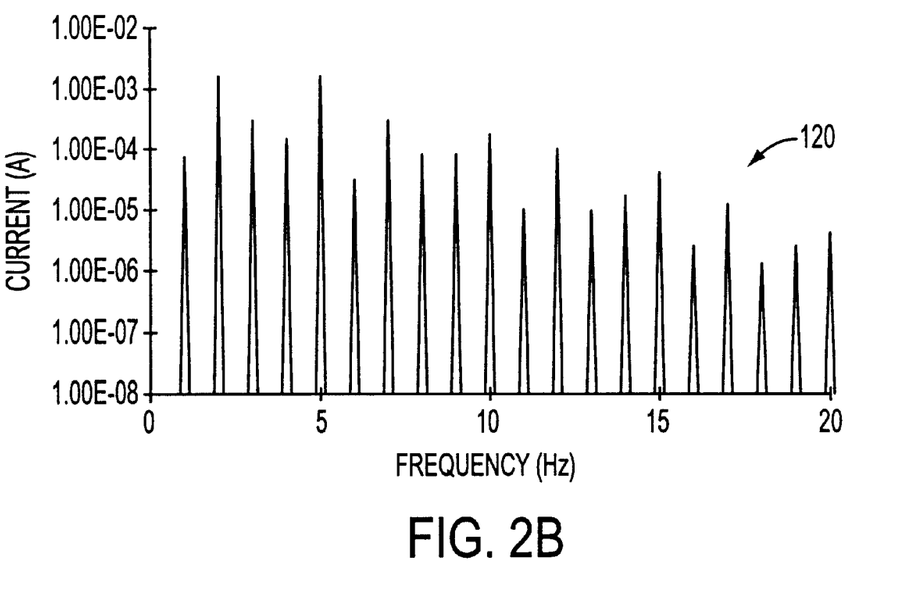

This perturbation signal 110 is then applied to a corroding system 130, generating a response current 120 in response to the signal. The relationship between the perturbation signal 110 applied and the response current 120, i, is shown schematically in FIG. 1B (in the time domain) and in FIG. 1C (in the frequency domain), and is mathematically described by the following equation:

$$i = i_{corr}\left[\exp\left((ln10)E - \frac{E_{coor}}{b_a}\right) - \exp\left(-\left(ln10 E - \frac{E_{corr}}{b_c}\right)\right)\right] \quad (1.2)$$

where $i_{corr}$ is the corrosion current density (and is unknown), E the potential of the applied perturbation signal 110, $E_{corr}$ the measured corrosion potential, $b_a$ the anodic Tafel parameter and $b_c$ the cathodic Tafel parameter. The response current 120 is measured at zero, harmonic and intermodulation frequencies and then analyzed in accordance with the method of the present invention to obtain the corrosion rate. For example, FIGS. 2A and 2B are computer simulations of the response current 120 generated in a corroding system 130 in response to a perturbation signal 110 having an amplitude ($U_o$) of 20 mV and sinusoidal components of 2 and 5 Hz. ($f_1$=2 Hz and $f_2$=5 Hz). Analyzing the response current 120 shown in the computer simulation of FIGS. 2A and 2B using equation 1.2 yields $i_{corr}$=1.10$^{-3}$ A/cm$^2$, $b_a$=60 mV/dec and $b_c$=120 mV/dec.

Figure 3:
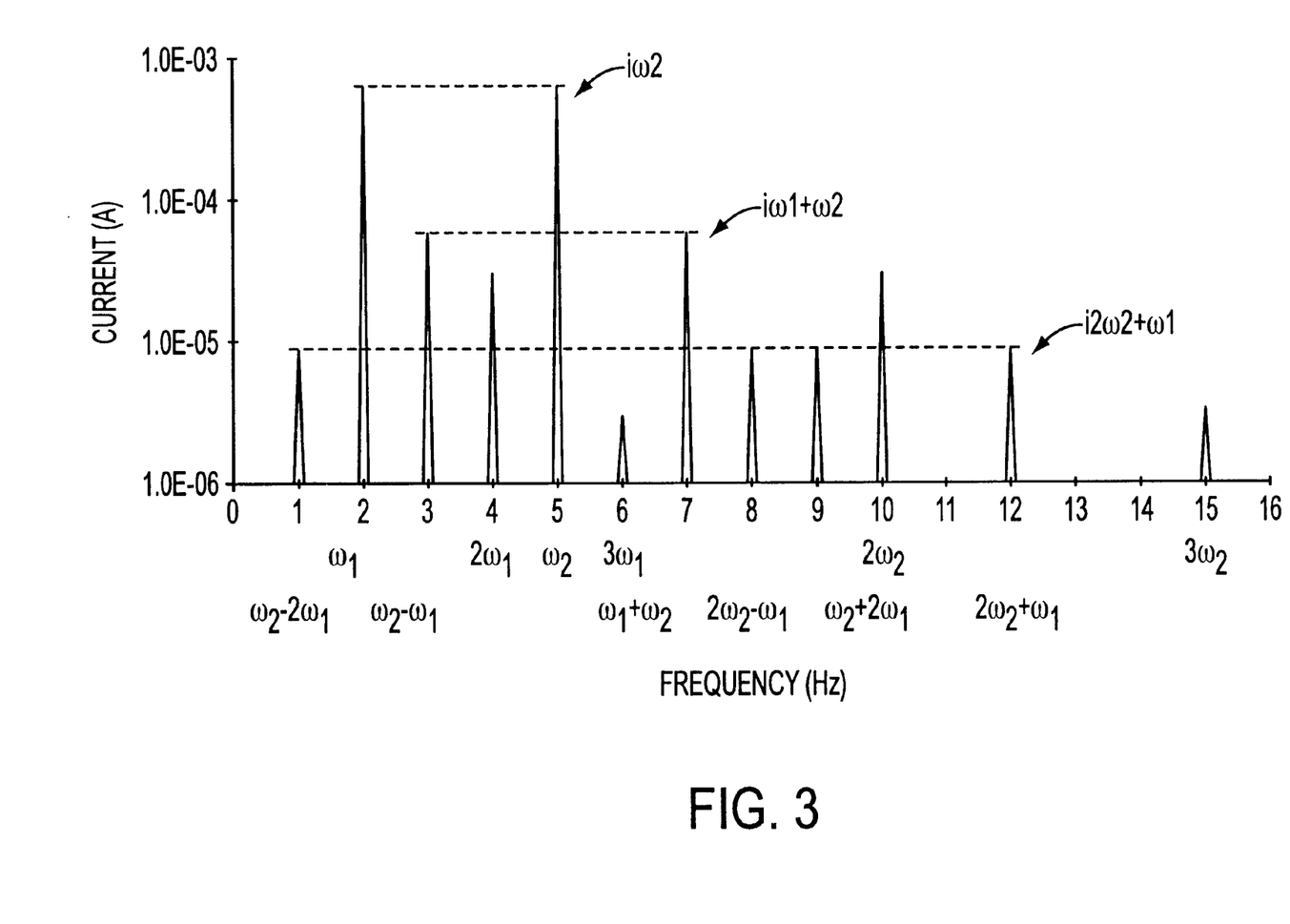
FIG. 3 is a graph of response current in amperes generated in a corroding system in response to applied signals at applied, harmonic and intermodulation frequencies.

A computer simulation of a frequency spectrum of the response current 120 at different harmonic and intermodulation frequencies, is shown in FIG. 3.

Figure 4:
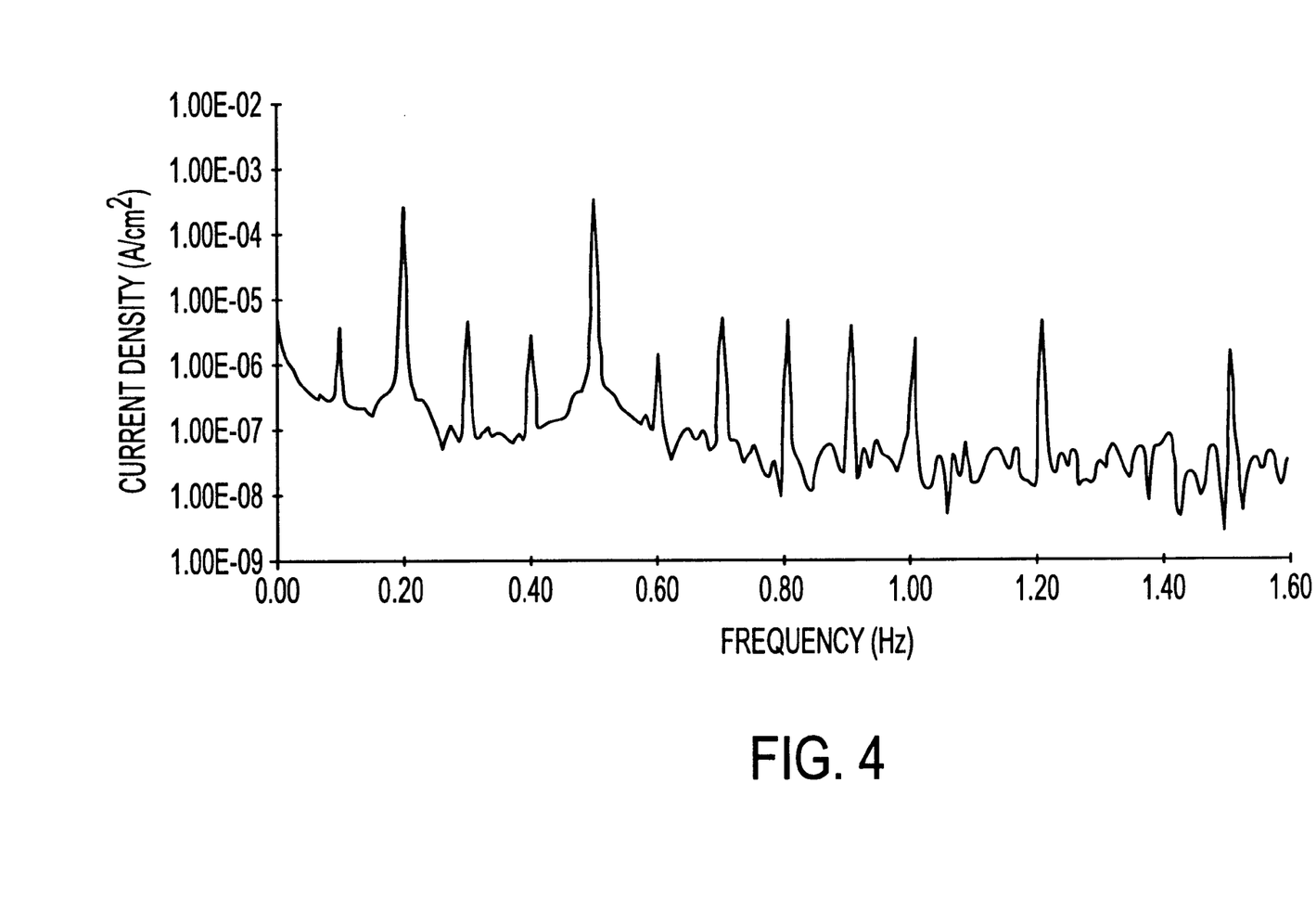
FIG. 4 is a graph of current density of response current in amperes per square centimeter generated in a corroding system in response to applied signals at applied, harmonic and intermodulation frequencies.

A typical result for a real corroding system 130, i.e., mild steel in sulfuric acid solution, obtained using a perturbation signal 110 with an amplitude of 20 mV and frequencies of 0.2 and 0.5 Hz, is shown in FIG. 4. The choice for the frequencies of 0.2 and 0.5 Hz was based on two requirements. First, the harmonics and intermodulation frequencies should not interfere with one another. Second, the frequencies should be sufficiently low to minimize the effect of capacitive behavior of the system, and sufficiently high to reduce the time needed to perform a measurement. The frequencies chosen are a compromise to meet both requirements. (An exemplary calculation of corrosion rate and Tafel parameters based on the frequency spectrum shown in FIG. 4 is given infra and the intermodulation components of the response current 120 are summarized in Table 1 and the corresponding corrosion rates given in Table 2.)

Figure 5:
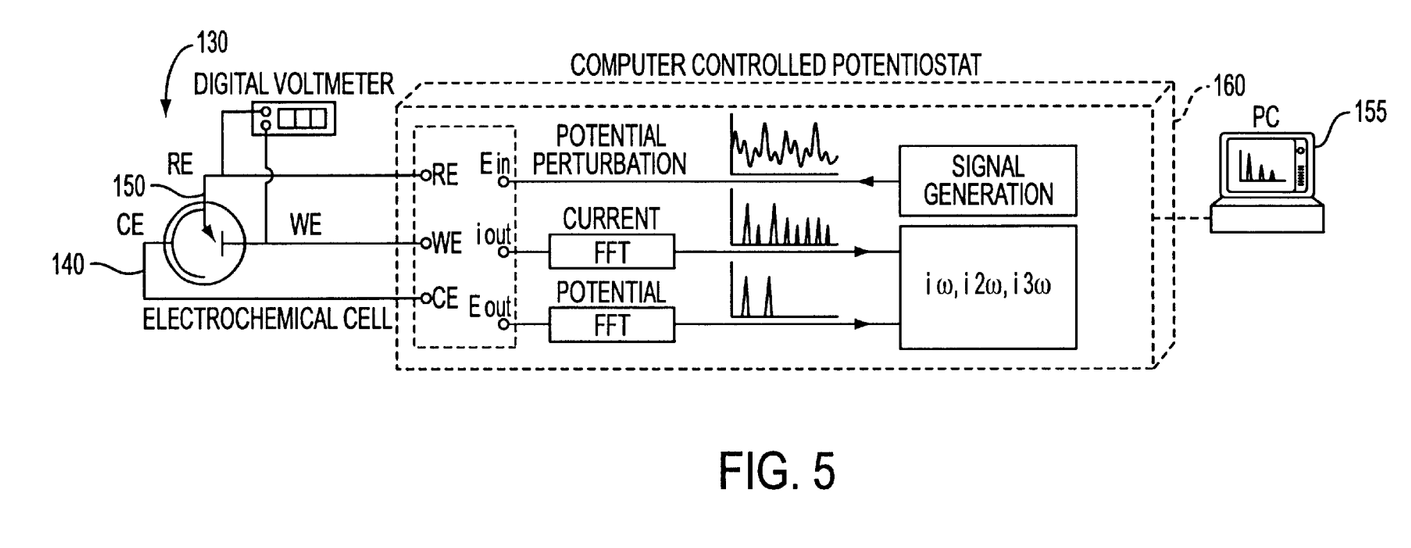
FIG. 5 is an embodiment of an experimental set-up suitable for performing EFM measurements according to the present invention.

An embodiment of a test set-up suitable for performing the EFM technique of the present invention is shown in FIG. 5. The corroding system 130 is represented by an electrochemical cell 135 having a counter electrode 140, a working electrode 145 and a reference electrode 150. The test set-up generally includes a computer 155 with a computer program (not shown) stored therein, and a computer controlled potentiostat 160, such as a Gamry PC-750, commercially available from Gamry Instruments Inc., of Warminster, Pa. Preferably, to facilitate displaying results of the EFM-technique, the computer program is written using a graphical programming language such as LabVEW, commercially available from National Instruments Corporation, of Austin, Tex. Generally, the computer program includes a sinewave-generator module for generating and applying a perturbation signal 110 having two or more sinusoidal signals 100, 105, of different frequencies to the corroding system 130. A measured-waveform module measures the voltage of the perturbation signal 110 and the resulting response current 120 generated in the system 130 in response to the perturbation signal. A frequency-response-magnitude module transforms the measured response current 120 from the time domain to the frequency domain. A frequency-response-analyzer module analyzes the response current 120 to obtain the corrosion rate.

In operation, corrosion potential of the electrochemical cell 135 is measured using a digital voltmeter 165 and the potentiostat 160 is set to this value. A perturbation signal 110 is then generated by the computer 155 and fed to the potentiostat 160. The response current 120 is then measured by the potentiostat 160 and then analyzed by the computer 155. The response current 120 is then transformed to the frequency domain by the frequency-response-magnitude module using a Fourier Transform. Then the response currents 120 at the frequencies of interest are selected and saved to a storage media (not shown) in the computer 155, for later calculation of the corrosion rate by the frequency-response-analyzer module.

A method of monitoring the corrosion rate of an activation controlled corroding system 130 will now be described. A perturbation signal 110 consisting of two sinusoidal signals 100, 105, of different frequencies is applied to the system 130 such that:

$$\eta = U_o \sin \omega_1 t + U_o \sin \omega_2 t \quad (3.1)$$

where $\eta$ is an overpotential applied to the system, $U_o$ the amplitude of the perturbation signal, t is time and $\omega_1$ and $\omega_2$ are the angular frequencies of the sinusoidal signals in rad/s.

Note that the frequencies making up the perturbation signal 110 can also be expressed in Hertz where $\omega = 2\pi f$. Because the corroding process is non-linear in nature, the response current 120 due to the perturbation signal 110 contains non-linear components. That is the frequency spectrum of the response current 120 will include components at harmonics or multiples of the frequencies of the two sinusoidal signals 100, 105, ($\omega_1, 2\omega_1, 3\omega_1, \ldots, \omega_2, 2\omega_2, 3\omega_2, \ldots$), and at the intermodulation frequencies ($\omega_1 \pm \omega_2, 2\omega_1 \pm \omega_2, 2\omega_2 \pm \omega_1 \ldots$). The corrosion rate and Tafel parameters are obtained by analyzing the response current 120 of these components at different frequencies. The derivation of an equation for analyzing the response current 120 starts with a current-potential equation modeling a corroding process following the Tafel law:

$$i = i_{corr}\left[\exp\left(\frac{\eta}{\beta_a}\right) - \exp\left(\frac{\eta}{\beta_c}\right)\right] \quad (3.2)$$

where $i_{corr}$ is the corrosion current density, $\beta_a$ the anodic Tafel parameter and $\beta_c$ the cathodic Tafel parameter. Notice that $\beta_a = b_a/\ln 10$ and $\beta_c = b_c/\ln 10$. Throughout the text $\beta_a$ and $\beta_c$ will be used when mathematical modeling is carried out to avoid repeating the factor ln10 over and over again. For numerical simulation the $b_a$ and $b_a$ values are used, because they are more common (compare $\beta_c = 120$ mV/dec with $b_c = 52.1$ mV). Substituting the perturbation signal 110 described with equation (3.1) into equation (3.2) yields:

$$i = i_{corr}\left[\exp\left(\frac{U_o \sin \omega_1 t}{\beta_a}\right)\exp\left(\frac{U_o \sin \omega_2 t}{\beta_a}\right) - \exp\left(-\frac{U_o \sin \omega_1 t}{\beta_c}\right)\exp\left(-\frac{U_o \sin \omega_2 t}{\beta_c}\right)\right] \quad (3.3)$$

Expanding the exponential parts using a Taylor series expansion:

$$\exp\left(\frac{U_o \sin \omega_1 t}{\beta_a}\right) = \quad (3.4)$$

$$1 + \frac{U_o \sin \omega_1 t}{\beta_a} + \frac{1}{2}\left(\frac{U_o \sin \omega_1 t}{\beta_a}\right)^2 + \frac{1}{6}\left(\frac{U_o \sin \omega_1 t}{\beta_a}\right)^3 + \ldots$$

and:

$$\exp\left(-\frac{U_o \sin \omega_1 t}{\beta_c}\right) = \quad (3.5)$$

$$1 - \frac{U_o \sin \omega_1 t}{\beta_c} + \frac{1}{2}\left(\frac{U_o \sin \omega_1 t}{\beta_c}\right)^2 - \frac{1}{6}\left(\frac{U_o \sin \omega_1 t}{\beta_c}\right)^3 + \ldots$$

For the exponential parts $$\exp\left(\frac{U_o \sin \omega_2 t}{\beta_a}\right)$$

and $$\exp\left(-\frac{U_o \sin \omega_2 t}{\beta_c}\right)$$

an analogue treatment is valid. Following trigonometric relationships, equation (3.3) is written as a series of sines and cosines with different frequencies:

$$\left(\frac{U_o \sin\omega_1 t}{\beta_a}\right) = \frac{1}{2}\left(\frac{U_0}{\beta_a}\right)^2 - \frac{1}{2}\left(\frac{U_0}{\beta_a}\right)^2 \cos 2\omega_1 t \quad (3.6)$$

and:

$$\left(\frac{U_o \sin\omega_1 t}{\beta_a}\right) = \frac{3}{4}\left(\frac{U_0}{\beta_a}\right)^3 \sin\omega_1 t - \frac{1}{4}\left(\frac{U_0}{\beta_a}\right)^2 \sin 2\omega_1 t \quad (3.7)$$

These relationships are also used for the terms with $\omega_2$ and $\beta_c$. Using the Taylor-series expansion for exp(x) to the third order and some algebraic manipulations, yields an equation of the following form:

$i = i_{fr} + i_{\omega 1} \sin \omega_1 t + i_{\omega 2} \sin \omega_2 t - i_{2\omega 1} \sin 2\omega_1 t - i_{2\omega 2} \sin$ $2\omega_2 t - i_{3\omega 1} \sin 3\omega_1 t - i_{3\omega 2} \sin 3\omega_2 t + i_{\omega 2 \pm \omega 1} \cos(\omega_2 t - \omega_1 t) - i_{w2 \pm \omega 1}$
$\cos(\omega_2 t - \omega_1 t)$ $+ i_{2\omega 2 \pm \omega 1} \sin(2\omega_2 t - \omega_1 t) - i_{2\omega 2 \pm \omega 1} \sin(2\omega_2 t + \omega_1 t) + i_{2w1 \pm \omega 2}$ $\sin(2\omega_1 t - \omega_2 t) + i_{2\omega 1 \pm \omega 2} \sin(2\omega_1 t + \omega_2 t)$  (3.8)

where $i_{fr}$ is the Faraday rectification current, $i_{\omega 1}$ and $i_{\omega 2}$ are the response currents 120 at frequency $\omega_1$, and $\omega_2$, respectively, $i_{\omega 2+\omega 1}$ and $i_{\omega 2-\omega 1}$ are the response currents 120 at intermodulation frequency $\omega 2+\omega 1$ and $\omega 2-\omega 1$, etc. Collecting terms with the same frequency and solving for $i_{corr}$ and $\beta_a$ and $\beta_c$ the following expressions are obtained, assuming that $\omega_2$ is larger than $\omega_1$, (and $\beta_a < \beta_c$):

$$i_{corr} = \frac{i_{\omega 1 \omega 2}^2}{2\sqrt{8 i_{\omega 1 \omega 2} i_{\omega 2 \pm w 1} - 3 i_{\omega 2 \pm \omega 1}^2}}, \quad (3.9)$$

$$\beta_a = \frac{i_{\omega 1 \omega 2} U_0}{i_{\omega 2 \pm \omega 1} + \sqrt{8 i_{\omega 1 \omega 2} i_{\omega 2 \pm w 1} - 3 i_{\omega 2 \pm \omega 1}^2}}, \quad (3.10)$$

$$\beta_c = \frac{i_{\omega 1 \omega 2} U_0}{-1_{\omega 2 \pm \omega 1} + \sqrt{8 i_{\omega 1 \omega 2} i_{\omega 2 \pm w 1} - 3 i_{\omega 2 \pm \omega 1}^2}}, \quad (3.11)$$

where the intermodulation components of the response current 120 are obtained from the frequency spectrum shown in FIG. 3. These equations can be used to calculate a corrosion rate, when both the anodic and cathodic reactions are under activation control (i.e., when they follow Tafel behavior).

These equations are valid when the amplitude of the perturbation signal 110 is smaller than the Tafel parameters, i.e. when $U_o/\beta_a \ll 1$ and $U_o/\beta_c \ll 1$. If a perturbation signal 110 having a larger amplitude is desired, for instance due to excessive background noise, the mathematical modeling should be carried out with a modified Bessel function, i.e., the Taylor expansions of equations (3.4) and (3.5) are replaced by an expansion with a modified Bessel function. (See EPRI-report WO 8041-09, paragraph 3.5.1, incorporated heerin by reference.)

A method of monitoring the corrosion rate of a diffusion controlled corroding system 130 will now be described. For a corrosion process in which the cathodic reaction is completely controlled by diffusion, the cathodic Tafel parameter is infinite. ($\beta_c \to \infty$). The current-potential relation corresponding with this situation is:

$$i = i_{corr}\left[\exp\left(\frac{\eta}{\beta a}\right) - 1\right] \quad (3.12)$$

Substituting the perturbation signal 110 described with equation (3.1) into equation (3.12) and using an analogue treatment as before, yields the following equations for calculating a corrosion rate ($i_{corr}$), and the anodic Tafel parameter ($\beta_a$) when the cathodic reaction is diffusion controlled.

$$i_{corr} = \frac{i_{\omega 1 \omega 2}^2}{2 i_{\omega 2 \pm \omega 1}} \quad (3.13)$$

$$\beta_a = \frac{i_{\omega 1 \omega 2}}{2 i_{\omega 2 \pm \omega 1}} U_o \quad (3.14)$$

A method of monitoring the corrosion rate of a passivation controlled corrosion system 130 will now be described. For a corrosion process in which anodic reaction is completely passivated, the anodic Tafel parameter is infinite ($\beta_a \to \infty$). The current-potential relation corresponding to this situation is:

$$i = i_{corr}\left[1 - \exp\left(-\frac{\eta}{\beta_c}\right)\right] \quad (3.15)$$

The perturbation signal 110 of equation (3.1) is substituted in equation (3.15) and, after an analogue treatment as before, the following equations are obtained for calculating a corrosion rate ($i_{corr}$), and the cathodic Tafel parameter ($\beta_c$):

$$i_{corr} = \frac{i_{\omega 1 \omega 2}^2}{2 i_{\omega 2 \pm \omega 1}} \quad (3.16)$$

$$\beta_c = \frac{i_{\omega 1 \omega 2}}{2 i_{\omega 2 \pm \omega 1}} U_o \quad (3.17)$$

A method of monitoring the corrosion rate of a corroding system 130 under cathodic protection assuming that the anodic and cathodic reactions following Tafel behavior will now be described. To derive intermodulation equation for a polarized system equation (3.2) is again used.

$$i = i_{corr}\left[\exp\left(\frac{\bar{\eta}}{\beta_a}\right) - \exp\left(\frac{\bar{\eta}}{\beta_c}\right)\right] \quad (3.2')$$

where $\bar{n}$ is the overpotential containing both DC and AC components. The potential perturbation signal 110 for the intermodulation technique:

$\eta = \eta + U_o \sin \omega_1 t + U_o \sin \omega_2 t$  (3.18)

is substituted in equation (3.2') resulting in:

$$i = i_{corr}\left[\exp\left(\frac{\eta}{\beta_a}\right)\exp\left(\frac{U_o \sin\omega_1 t + U_o \sin\omega_2 t}{\beta_a}\right) - \exp\left(\frac{\eta}{\beta_c}\right)\exp\left(\frac{-U_o \sin\omega_1 t + U_o \sin\omega_2 t}{\beta_c}\right)\right] \quad (3.19)$$

This equation is expanded according to equations (3.4) and (3.5). After some mathematical rearrangements the following equations for the intermodulation components of the response current 120 are obtained:

$$i_{\omega 1 \omega} = i_{corr}\left(\exp\left(\frac{\eta}{\beta_a}\right)\left(\frac{U_o}{\beta_a}\right) + \exp\left(-\frac{\eta}{\beta c}\right)\left(\frac{U_o}{\beta_c}\right)\right) \quad (3.20)$$

$$i_{\omega 2 \pm \omega 1} = \frac{1}{2}i_{corr}\left(\exp\left(\frac{\eta}{\beta_a}\right)\left(\frac{U_o}{\beta_a}\right)^2 - \exp\left(-\frac{\eta}{\beta_c}\right)\left(\frac{U_o}{\beta_c}\right)^2\right) \quad (3.21)$$

-continued $$i_{2\omega2\pm\omega1} = \frac{1}{8}i_{corr}\left(\exp\left(\frac{\eta}{\beta_a}\right)\left(\frac{U_o}{\beta_a}\right)^3 + \exp\left(-\frac{\eta}{\beta_c}\right)\left(\frac{U_o}{\beta_c}\right)^3\right) \quad (3.22)$$

These are three equations with four unknowns ($i_{corr}$, $\beta_a$, $\beta_c$ and $\eta$). To solve this set of equations at least one of the unknowns must be known. One approach is to use an estimated value for the potential $\eta$, and solve the three non-linear equations by the Levenberg-Marquardt method using a computer program such as MathCad®. Proper estimation of the initial values is necessary to avoid problems with root-finding. It has been found that this can be accomplished by using the solution of the first set of experimental data as the initial values for the second set of experimental data, and then the second set of experimental data for the third etc . . .

In another aspect, the present invention is directed to a method of validating the quality of the data used in calculating the corrosion rate, and in particular validating measurements made of the response current 120 and voltage or potential of the perturbation signal 110. As noted above, the frequency spectrum of the response current 120 contains components at harmonic and intermodulation frequencies of the applied perturbation signal 110. The harmonic components $i_{2\omega1}$ and $i_{2\omega2}$, are measured at frequencies $2\omega_1$ and $2\omega_2$. The harmonic components $i_{3\omega1}$ and $i_{3\omega2}$, are measured at frequencies $3\omega_1$ and $3\omega_2$. The intermodulation components $i_{\omega2\pm\omega1}$ are measured at frequencies $\omega_2\pm\omega_1$ and the intermodulation components $i_{2\omega2\pm\omega1}$ and $i_{2\omega1\pm\omega2}$ are measured at frequencies $2\omega_2\pm\omega_2$ and $2\omega1\pm\omega2$ respectively. It has been found that between these components there exists a relationship such that:

$$i_{\omega2\pm\omega1}=2i_{2\omega1}=2i_{2\omega2} \quad (3.23)$$

and:

$$i_{2\omega2\pm\omega1}=i_{2\omega1\pm\omega2}=3i_{3\omega1}=3i_{3\omega2} \quad (3.24)$$

These relationships are used to derive causality factors for validating the quality of the measured data, which are defined as:

Causality factor 2: $\dfrac{i_{\omega2\pm\omega l}}{i_{2\omega l}}$ (3.25)

Causality factor 3: $\dfrac{i_{\omega2\pm\omega l}}{i_{3\omega l}}$ (3.26)

The response current 120 components in equations (3.25) and (3.26) are interchangeable with the current components mentioned in equations (3.23) and (3.24). Thus, if there is a causal relation between the perturbation signal 110 and the response current 120, causality factor 2 is equal to two and causality factor 3 is equal to three. If the causality factors differ significantly from these theoretical values, it can be deduced that the measurements were influenced by noise and hence not valid. If on the other hand the causality factors are substantially equal to the predicted values of two and three, there is a causal relation between the perturbation signal 110 and the response current 120, and the measured data is assumed to be reliable.

EXAMPLES

The following examples illustrate advantages of a method and apparatus for monitoring the corrosion of corroding systems 130 according to the present invention. The examples are provided to illustrate certain embodiments of the present invention, and are not intended to limit the scope of the invention in any way.

The first example illustrates a method and apparatus for monitoring the corrosion of mild steel in a corroding system 130 having a sulfuric acid solution (0.05 M $H_2SO_4$). FIG. 4 shows the frequency spectrum of the response current 120 of this corroding system 130 due to a perturbation signal 110 of 20 mV and consisting of two sinusoidal signals having 100, 105, frequencies of 0.2 and 0.5 Hz. The response current 120 measured at zero, harmonic and intermodulation frequencies for this frequency spectrum is shown in Table 1 along with the corresponding frequencies.

TABLE I

| Current component | Angular frequency (rad/s) | Frequency (Hz) | Current density (A/cm$^2$) |
|---|---|---|---|
| $i_{\omega1\omega2}$ | $\omega_1$ | 0.2 | $3.19\times10^{-4}$ |
|  | $\omega_2$ | 0.5 | $3.19\times10^{-4}$ |
| $i_{\omega2\pm\omega1}$ | $\omega_2 - \omega_1$ | 0.3 | $4.89\times10^{-6}$ |
|  | $\omega_2 + \omega_1$ | 0.7 | $4.98\times10^{-6}$ |
| $i_{\omega2\pm\omega1}$ | $\omega_2 - 2\omega_1$ | 0.1 | $4.10\times10^{-6}$ |
|  | $2\omega_2 + \omega_1$ | 0.8 | $4.30\times10^{-6}$ |
|  | $\omega_2 + 2\omega_1$ | 0.9 | $4.21\times10^{-6}$ |
|  | $2\omega_2 + \omega_1$ | 1.2 | $4.17\times10^{-6}$ |
| $i_{2\omega1}$ | $2\omega_1$ | 0.4 | $2.76\times10^{-6}$ |
| $i_{2\omega2}$ | $2\omega_2$ | 1.0 | $2.24\times10^{-6}$ |
| $i_{3\omega1}$ | $3\omega_1$ | 0.6 | $1.44\times10^{-6}$ |
| $i_{3\omega2}$ | $3\omega_2$ | 1.5 | $1.35\times10^{-6}$ |

These data were then used to calculate the corrosion current density, the Tafel parameters and the causality factors with equations (3.9), (3.10), (3.11), (3.25) and (3.26) respectively. Harmonic and intermodulation current components measured at multiple frequencies are averaged, for example $i_{3\omega1}$ and $i_{2\omega2\pm\omega1}=i_{2\omega1\pm\omega2}$ follow from:

$$i_{3\omega1} = \frac{1.44\cdot10^{-6} + 1.35\cdot10^{-6}}{2} = 1.39\cdot10^{-6}$$

$$i_{2\omega1} = \frac{4.1\cdot10^{-6} + 4.3\cdot10^{-6} + 4.21\cdot10^{-6} + 4.17\cdot10^{-6}}{4}$$

$$= 4.20\cdot10^{-6}$$

The Causality factor 3 is then calculated as follows:

$$\text{Causality factor 3:} \frac{i_{2\omega2\pm\omega1}}{i_{3\omega1}} = \frac{4.20\cdot10^{-6}}{1.39\cdot10^{-6}} = 3.01$$

And the result shown in Table II.

TABLE II

| Parameter | Value |
|---|---|
| Corrosion current density (A/cm$^2$) | $4.93 \times 10^{-4}$ |
| Anodic Tafel parameter (mV/dec) | 135 |
| Cathodic Tafel parameter (mV/dec) | 149 |
| Causality factor 2 | 1.97 |
| Causality factor 3 | 3.01 |

Figure 6:
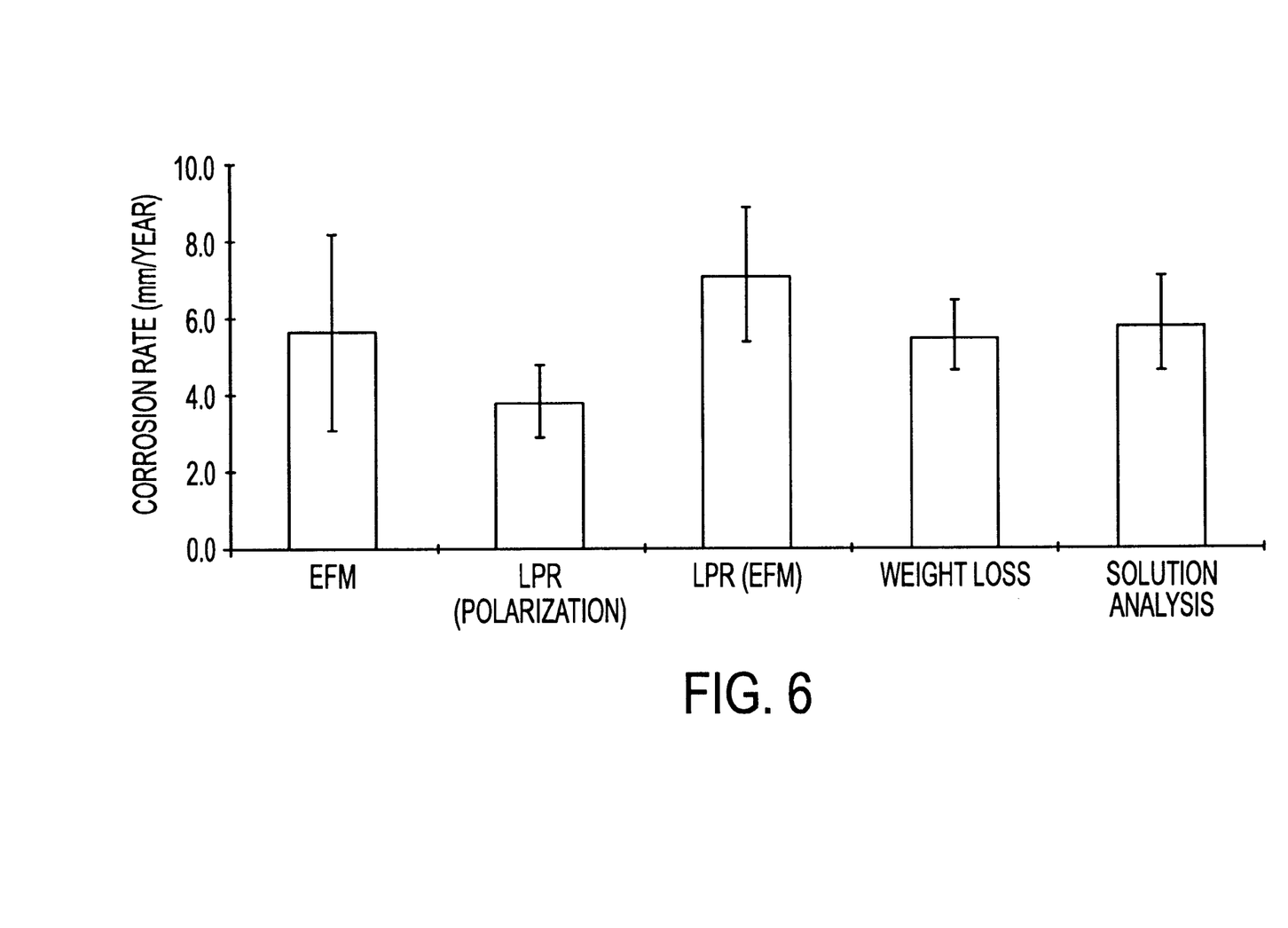
FIG. 6 is a graph comparing corrosion rates for a corroding system of mild steel in 0.05 M $H_2SO_4$ determined using conventional methods and an EFM-technique according to the present invention.

The causality factors indicate that the measured data are of good quality. Moreover, as shown in FIG. 6, the calculated corrosion rate is in good agreement with other techniques. FIG. 6 shows a comparison of corrosion rates obtained for the same corroding system with the EFM-technique, LPR polarization, LPR EFM, weight loss and solution analysis, thereby validating the EFM-technique of the present invention.

Figure 7:
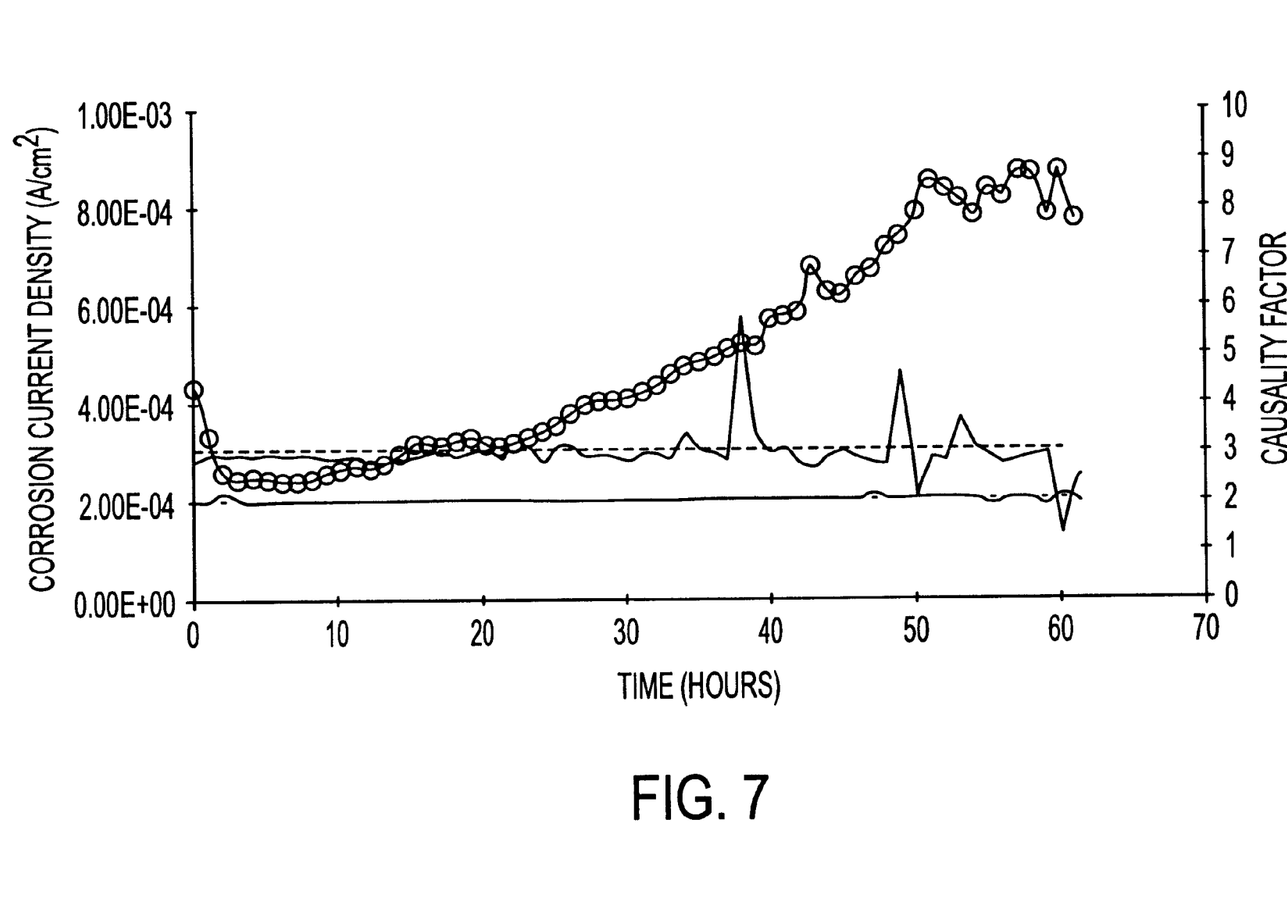
FIG. 7 are graphs of corrosion current density and causality factors for a corroding system of mild steel in 0.05 M $H_2SO_4$ determined using an EFM-technique according to the present invention.

The EFM-technique of the present invention has been used to measure corrosion rates of various other corroding systems. FIG. 7 shows corrosion rates measured with the EFM-technique of mild steel in a 0.05 M $H_2SO_4$ solution open to the air. The corrosion rate is slightly increasing with time. The causality factors both confirmed the quality of the experimental data throughout the experiment. A few suspicious data points can be distinguished, where the causality factor three deviates from its reference value 3.

Figure 8:
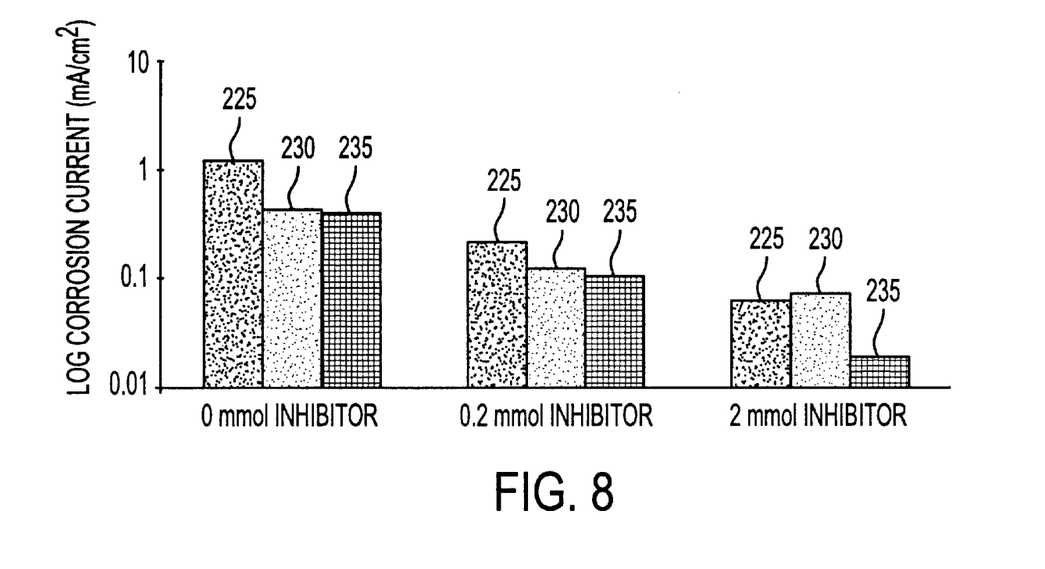
FIG. 8 is a graph comparing corrosion rates obtained with the EFM technique, EIS, and polarization curves (Tafel extrapolation) in an acidic environment with various inhibitor concentrations.

FIG. 8 shows an example where corrosion rates are measured for a corroding system comprising mild steel in a solution of 0.05 M $H_2SO_4$ with different inhibitor concentrations. The results obtained with the EFM technique 225, EIS 230, and polarization curves 235 (Tafel extrapolation) show similar behavior, again validating the EFM-technique.

Figure 9:
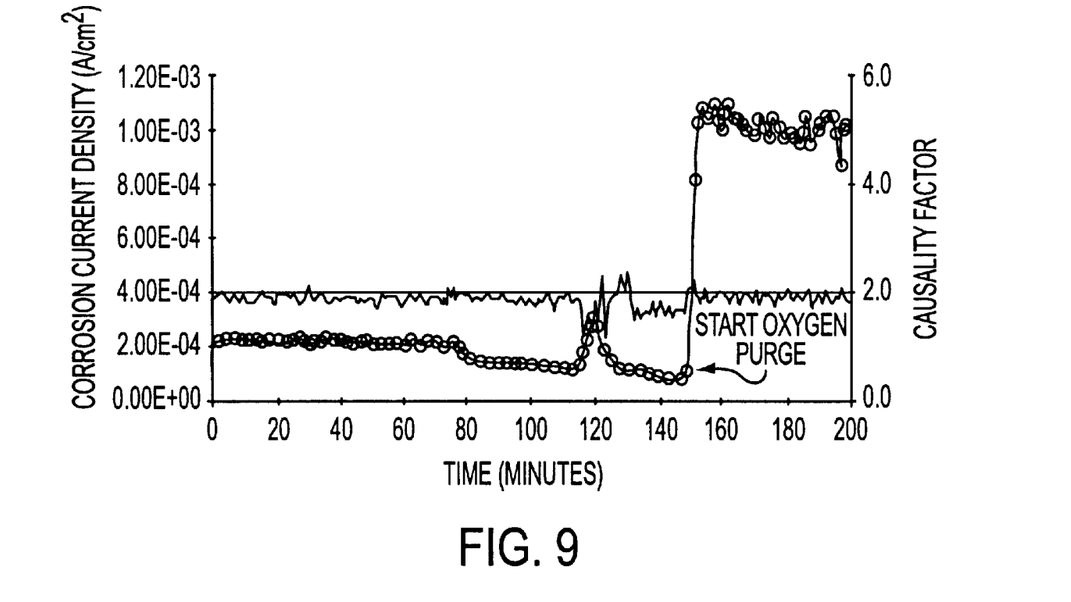
FIG. 9 are graphs of corrosion rates obtained with the EFM-technique for mild steel in 0.5 M NaCl under different aeration conditions.

FIG. 9 shows a typical on-line corrosion monitoring result, where the measured corrosion rates are influenced by variations in oxygen concentrations. This result shows both that the EFM-technique is capable of on-line measuring changes in the corrosion rate and that the causality factor can clearly distinguish between good and bad data points.

Figure 10:
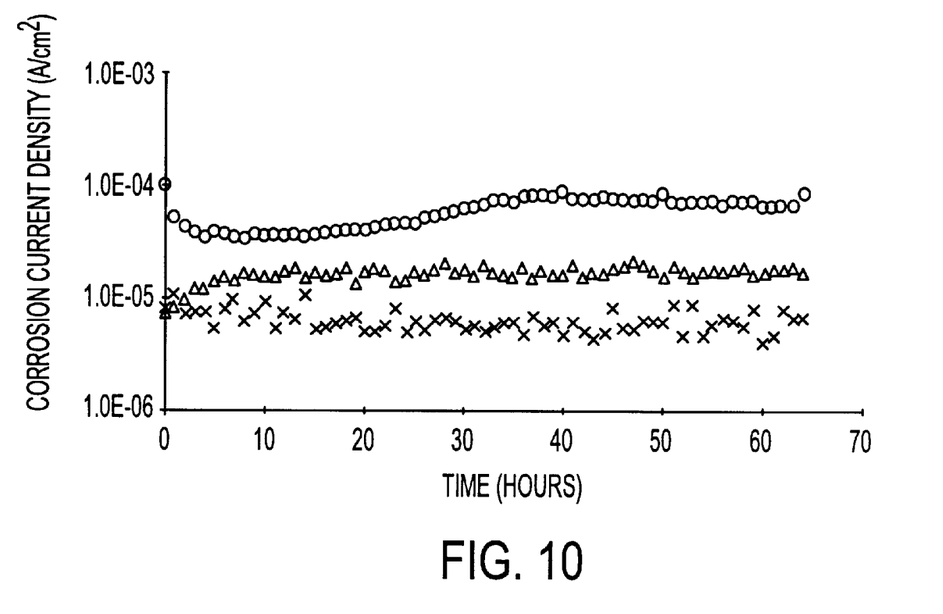
FIG. 10 shows corrosion rates determined with the EFM-technique solving three non-linear equations for mild steel in 0.5 M NaCl at the corrosion potential, at −650 mV and at −700 mV versus the reference electrode (Ag/AgCl, 3 M KCl)
Figure 11:
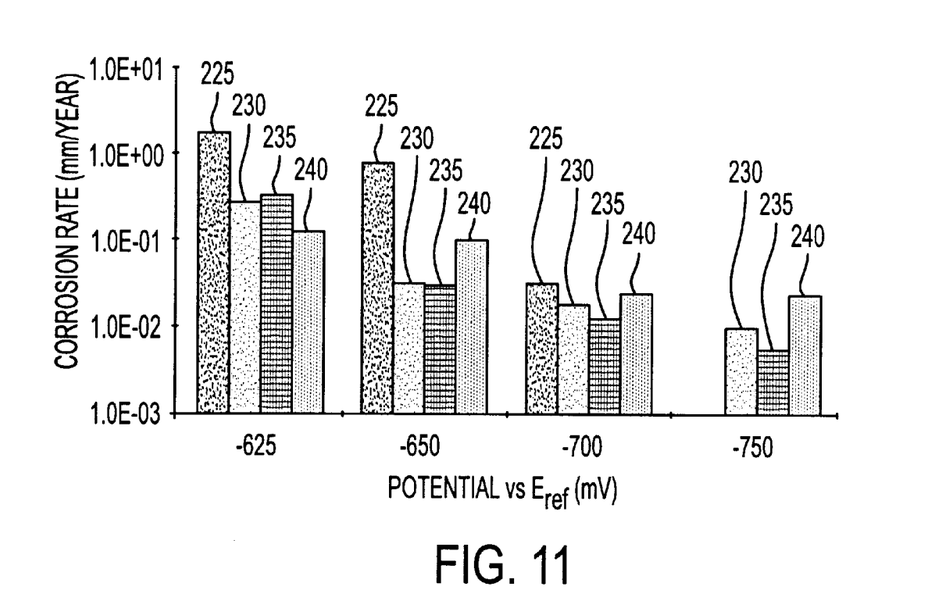
FIG. 11 is a graph comparing corrosion rates obtained with the EFM technique, EIS, Tafel extrapolation and weight loss measurements for different cathodic potentials.

FIG. 10 shows corrosion rates determined using the EFM-technique of the present invention at various cathodic potentials. It shows clearly that increasing cathodic polarization decreases the corrosion rate. FIG. 11 shows a comparison with other corrosion monitoring techniques including a weighing technique 240 wherein the corrosion rate is determined by weighing the corroded metal before after corrosion takes place.

It is to be understood that even though numerous characteristics and advantages of certain embodiments of the present invention have been set forth in the foregoing description, together with details of the structure and function of various embodiments of the invention, this disclosure is illustrative only, and changes may be made in detail, especially in matters of structure and arrangement of parts within the principles of the present invention to the full extent indicated by the broad general meaning of the terms in which the appended claims are expressed.

What is claimed is:

1. A method of monitoring a corrosion current density to determine a corrosion rate of a corroding system, the method comprising steps of:
   (a) applying two sinusoidal signals having different frequencies to a portion of the system, the two sinusoidal signals have angular frequencies $\omega_1$ and $\omega_2$;
   (b) measuring a response current in response to the sinusoidal signals; and
   (c) analyzing the response current measured at zero, harmonic and intermodulation frequencies to obtain the corrosion rate by:
      (i) transforming the response current from a time domain to a frequency domain; and
      (ii) calculating the corrosion current density ($i_{corr}$) using the following equation:

$$i_{corr} = \frac{i_{\omega I \omega 2}^2}{2 i_{\omega 2 \pm \omega I}}.$$

2. A method according to claim 1 wherein the corroding system is diffusion controlled and wherein the method further comprises the step of analyzing the response current to obtain an anodic Tafel parameter using the following equation:

$$\beta_a = \frac{i_{\omega I \omega 2}}{2 i_{\omega 2 \pm \omega I}} U_o.$$

3. A method according to claim 1 wherein the corrosion system is passivation controlled and wherein the method further comprises the step of analyzing the response current to obtain a cathodic Tafel parameter using the following equation:

$$\beta_c = \frac{i_{\omega I \omega 2}}{2 i_{\omega 2 \pm \omega I}} U_o.$$

4. A method according to claim 1 further comprising the step of (d) analyzing the measured response current to validate the quality of the measurements made in step (b).

5. A method according to claim 4 wherein the step of analyzing the measured response current to validate the quality of the measurements comprises the steps of:
   (d)(i) calculating a causality factor using the response current measured at an intermodulation frequency and at a harmonic frequency of one of the two applied sinusoidal signals; and
   (d)(ii) comparing the causality factor to a predetermined value.

6. A method according to claim 5 wherein the predetermined value is 2, and wherein step (d)(i) comprises the step of calculating the causality factor using the following equation:

$$\frac{i_{\omega 2 \pm \omega I}}{i_{2 \omega I}}.$$

7. A method according to claim 5 wherein the predetermined value is 3, and wherein step (d)(i) comprises the step of calculating the causality factor using the following equation:

$$\frac{i_{\omega 2 \pm \omega I}}{i_{3 \omega I}}.$$

8. A method of validating data measured to determine a corrosion rate of a corroding system, the method comprising steps of:
   (a) applying two sinusoidal signals having different frequencies to a portion of the system;
   (b) measuring a response current in response to the sinusoidal signals at harmonic and intermodulation frequencies;
   (c) calculating a causality factor using the response current measured at an intermodulation frequency and at a harmonic frequency of one of the two applied sinusoidal signals; and
   (d) comparing the causality factor to a predetermined value to validate the response current measured.

9. A method according to claim 8 wherein the predetermined value is 2, and wherein step (c) comprises the step of calculating the causality factor using the following equation:

$$\frac{i_{\omega 2\pm\omega 1}}{i_{2\omega 1}}.$$

10. A method according to claim 8 wherein the predetermined value is 3, and wherein step (c) comprises the step of calculating the causality factor using the following equation:

$$\frac{i_{\omega 2\pm\omega 1}}{i_{3\omega 1}}.$$

11. A computer program for monitoring a corrosion current density to determine a corrosion rate of a controlled corrosion system, the computer program comprising:

(a) a sinewave-generator module configured to generate and apply at least two sinusoidal signals having different frequencies to a portion of the system;

(b) a measured-waveform module configured to measure voltages of the sinusoidal signals and a response current generated in the system in response to the sinusoidal signals;

(c) a frequency-response-magnitude module configured to transform the measured response current from a time domain to a frequency domain; and (d) a frequency-response-analyzer module configured to analyze the response current measured at zero, harmonic and intermodulation frequencies of the sinusoidal signals to obtain the corrosion rate.

12. A computer program according to claim 11 wherein the sinewave-generator module generates two sinusoidal signals having angular frequencies of $\omega_1$ and $\omega_2$, and wherein the frequency-response-analyzer module is configured to calculate the corrosion current density ($i_{corr}$) using one of the following equations:

$$i_{corr} = \frac{i_{\omega 1 \omega 2}^2}{2\sqrt{8i_{\omega 1 \omega 2}i_{2\omega 2\pm w1} - 3i_{\omega 2\pm \omega 1}^2}}, \quad i_{corr} = \frac{i_{\omega 1 \omega 2}^2}{2i_{\omega 2\pm \omega 1}}.$$

13. A computer program according to claim 11 wherein the frequency-response-analyzer module is further configured to analyze the response current at harmonic and intermodulation frequencies of the sinusoidal signals to validate the quality of measurements made by the measured-waveform module.

14. A computer program according to claim 13 wherein the frequency-response-analyzer module is configured to:

(i) calculate a causality factor using the response current measured at an intermodulation frequency and at a harmonic frequency of one of the two applied sinusoidal signals; and (ii) compare the causality factor to a predetermined value to validate data quality.

15. A computer program according to claim 14 wherein the predetermined value is 2, and wherein the frequency response analyzer module is configured to calculate the causality factor using the following equation:

$$\frac{i_{\omega 2\pm\omega 1}}{i_{2\omega 1}}.$$

16. A computer program according to claim 14 wherein the predetermined value is 3, and wherein the frequency response analyzer module is configured to calculate the causality factor using the following equation:

$$\frac{i_{\omega 2\pm\omega 1}}{i_{3\omega 1}}.$$

17. A computer program according to claim 11 wherein the frequency-response-analyzer module is further configured to analyze the response current to obtain a Tafel parameter.

* * * * *